(12) United States Patent
Khalifa et al.

(10) Patent No.: US 11,719,094 B2
(45) Date of Patent: Aug. 8, 2023

(54) RESERVOIR CHARACTERIZATION USING ROCK GEOCHEMISTRY FOR LITHOSTRATIGRAPHIC INTERPRETATION OF A SUBTERRANEAN FORMATION

(71) Applicant: Saudi Arabian Oil Company, Dhahran (SA)

(72) Inventors: Aqeel M. Khalifa, Dhahran (SA); Edward A. Clerke, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 229 days.

(21) Appl. No.: 17/079,157

(22) Filed: Oct. 23, 2020

(65) Prior Publication Data

US 2022/0127959 A1   Apr. 28, 2022

(51) Int. Cl.
E21B 49/00 (2006.01)
E21B 49/02 (2006.01)
G01N 33/24 (2006.01)

(52) U.S. Cl.
CPC ............ E21B 49/005 (2013.01); E21B 49/02 (2013.01); G01N 33/24 (2013.01)

(58) Field of Classification Search
CPC ........ E21B 49/005; E21B 49/02; G01N 33/24
See application file for complete search history.

(56) References Cited

U.S. PATENT DOCUMENTS

| | | | |
|---|---|---|---|
| 4,661,701 A * | 4/1987 | Grau | G01V 5/101 376/160 |
| 8,217,337 B2 * | 7/2012 | Neville | G01V 5/04 324/303 |

(Continued)

FOREIGN PATENT DOCUMENTS

| | | |
|---|---|---|
| WO | 2013172948 | 11/2013 |
| WO | 2020046549 | 3/2020 |

OTHER PUBLICATIONS

Taher et al. "An Integrated Approach for Comprehensive Formation Evaluation in Mixed Lithologies using Source-Less Logging While Drilling and Advanced Cutting Analysis: A Case History," SPE-188573-MS (Year: 2017).*

Carugo et al., "Advanced Cuttings Analysis Improves Reservoir Characterisation and Reduces Operating Times in Shale Gas Drilling Project." International Petroleum Technology Conference, Mar. 2013, 15 pages.

(Continued)

Primary Examiner — John Fitzgerald
(74) Attorney, Agent, or Firm — Fish & Richardson P.C.

(57) ABSTRACT

An approach for reservoir characterization is based on rock geochemistry of the subterranean formation. This approach includes: collecting rock samples related to lithostratigraphy of target wells; measuring geochemical/ mineralogical parameters of the rock samples; measuring geochemical/ mineralogical parameters of the subsurface formation; measuring formation acoustic velocities for the target wells; generating characteristic rock sample and log signature patterns for different lithostratigraphic layers based on the measured geochemical/mineralogical parameters and acoustic velocities associated with the different lithostratigraphic layers identified in the target wells; combining the characteristic log signatures for the different lithostratigraphic layers into a lithographic interpretation using neutron capture spectroscopy model; and identifying the lithostratigraphic layers within the subterranean formation by applying the model to well logs of non-target wells.

16 Claims, 7 Drawing Sheets

(3 of 7 Drawing Sheet(s) Filed in Color)

(56) References Cited

U.S. PATENT DOCUMENTS

| | | | |
|---|---|---|---|
| 8,975,574 B2* | 3/2015 | Huiszoon | G01V 13/00 250/265 |
| 9,086,508 B2* | 7/2015 | Sinha | G01V 1/50 |
| 9,103,926 B2* | 8/2015 | Gzara | G01V 5/10 |
| 9,134,457 B2 | 9/2015 | Hurley et al. | |
| 9,501,740 B2* | 11/2016 | Hiu | G06N 3/08 |
| 9,541,668 B2* | 1/2017 | Grau | G01V 5/10 |
| 10,061,055 B2* | 8/2018 | Grau | G01V 5/104 |
| 10,209,389 B2* | 2/2019 | Gzara | G01N 24/08 |
| 10,365,261 B2 | 7/2019 | Montgomery et al. | |
| 10,385,677 B2* | 8/2019 | Gzara | E21B 43/00 |
| 10,394,976 B2 | 8/2019 | Adelinet | |
| 10,502,863 B2 | 12/2019 | Mosse et al. | |
| 10,534,871 B2 | 1/2020 | Pomerantz et al. | |
| 2004/0236513 A1* | 11/2004 | Tutuncu | G01V 1/50 702/11 |
| 2009/0248309 A1 | 10/2009 | Neville et al. | |
| 2013/0047717 A1* | 2/2013 | Gzara | G01V 5/10 73/152.05 |
| 2015/0218929 A1* | 8/2015 | Narasimhan | E21B 47/26 175/45 |
| 2016/0195636 A1* | 7/2016 | Grau | G01V 5/104 250/269.2 |
| 2018/0058211 A1* | 3/2018 | Liang | G01V 1/282 |
| 2018/0347321 A1 | 12/2018 | Hamon et al. | |
| 2019/0265373 A1* | 8/2019 | Ito | E21B 17/025 |
| 2019/0293815 A1 | 9/2019 | Jocker et al. | |
| 2020/0073012 A1 | 3/2020 | Frazer et al. | |
| 2020/0174145 A1 | 6/2020 | Sun et al. | |
| 2021/0102457 A1* | 4/2021 | Dupont | E21B 47/04 |

OTHER PUBLICATIONS

Qiang et al., "Prediction of reservoir quality from log-core and seismic inversion analysis with an artificial neural network: a case study from the Sawan gas field, Pakistan." Energies 13.2, Jan. 2020, 19 pages.

Yu et al., "Reservoir characterization and modeling: A look back to see the way forward." Jan. 2011, 289-309, 21 pages.

PCT International Search Report and Written Opinion in International Appln. No. PCT/US2021/056141, dated Jan. 21, 2022, 18 pages.

* cited by examiner

RESERVOIR CHARACTERIZATION USING ROCK GEOCHEMISTRY FOR LITHOSTRATIGRAPHIC INTERPRETATION OF A SUBTERRANEAN FORMATION

TECHNICAL FIELD

The present disclosure generally relates to reservoir characterization, particularly reservoir characterization by identification of lithostratigraphic layers within a subterranean formation based on rock geochemistry of the subterranean formation.

BACKGROUND

Lithostratigraphy is a sub-discipline of stratigraphy, the geological science associated with the study of strata or rock layers. Major focuses of lithostratigraphy include geochronology, comparative geology, and petrology.

Lithostratigraphic units are typically recognized and defined based on observable rock characteristics. The descriptions of strata based on physical appearance define facies. Lithostratigraphic units are only defined by lithic characteristics, and not by age. Lithostratigraphic units can include sedimentary layers that are laid down by deposition of sediment associated with weathering processes, decaying organic matters or through chemical precipitation and igneous layers which are plutonic or volcanic in character. Lithostratigraphic interpretation of a subterranean formation can be used to support identification of layers of the subterranean formation that are likely to have economically recoverable hydrocarbons.

SUMMARY

This specification describes an approach using geochemical and other rock measurements from rock samples in the laboratory including X-Ray diffraction, X-Ray fluorescence and inductively coupled plasma mass spectrometry in context of their pattern identification to perform lithostratigraphic interpretation. Based on these patterns, wellbore signals (e.g., neutron capture gamma ray spectroscopy, natural gamma ray spectroscopy and sonic acoustic velocity) are used to identify and interpret subsurface rock formations. This approach uses core-based sedimentological observations and links them to wellbore measurements in order to interpret lithostratigraphic intervals that are otherwise indistinguishable without core samples or biostratigraphy data.

This approach enables petrophysical explorations to distinguish between sedimentary deposits of economic viability with different age and variable reservoir characteristics that share similar rock properties in the subsurface when measured using conventional wellbore or lab measurements on the rocks. By reducing the need for capturing and retrieving rock samples to the surface, this approach can reduce the cost associated with core sampling and time consuming core sample analysis while expediting decisions that affect expensive drilling rig time and reducing the uncertainty for subsurface reservoir characterization and mapping associated with limited differentiation between formations with similar characteristics.

In one aspect, methods for reservoir characterization by identification of lithostratigraphic layers within a subterranean formation based on rock geochemistry of the subterranean formation include: collecting rock samples related to lithostratigraphy of target wells in the subterranean formation; measuring geochemical/mineralogical parameters of the rock samples with laboratory equipment; measuring geochemical/mineralogical parameters of the subsurface formation using wellbore geochemical logging tools in the target wells; measuring formation acoustic velocities for the target wells; generating characteristic rock sample and log signature patterns for different lithostratigraphic layers based on the measured geochemical/mineralogical parameters and acoustic velocities associated with the different lithostratigraphic layers identified in the target wells; combining the characteristic log signatures for the different lithostratigraphic layers into a lithographic interpretation using neutron capture spectroscopy (LINS) model; and identifying the lithostratigraphic layers within the subterranean formation by applying the LINS model to well logs of non-target wells.

In one aspect, methods for reservoir characterization by identification of lithostratigraphic layers within a subterranean formation based on rock geochemistry of the subterranean formation include: collecting rock samples related to lithostratigraphy of target wells in the subterranean formation; measuring formation acoustic velocities for the target wells; generating characteristic rock sample and log signature patterns for different lithostratigraphic layers based on the measured geochemical/mineralogical parameters and acoustic velocities associated with the different lithostratigraphic layers identified in the target wells; combining the characteristic log signatures for the different lithostratigraphic layers into a lithographic interpretation using neutron capture spectroscopy (LINS) model; and identifying the lithostratigraphic layers within the subterranean formation by applying the LINS model to well logs of non-target wells.

These methods can include one or more of the following features.

In some embodiments, collecting the lithostratigraphy of targeted wells in the subterranean formation comprises collecting core rock samples from at least some of the targeted wells. In some cases, collecting the lithostratigraphy of targeted wells in the subterranean formation comprises receiving previously measured lithostratigraphic profiles for previously drilled target wells.

In some embodiments, measuring geochemical or mineralogical parameters for the target wells comprises logging the target wells. In some cases, logging the target wells comprises using downhole logging tools to measure geochemical properties by natural and neutron activated gamma ray elemental spectrometry spectroscopy and acoustic slowness. In some cases, measuring geochemical or mineralogical parameters for the target wells further comprises performing analysis of rock samples taken from the target wells. In some cases, performing analysis of rock samples taken from the target wells comprises performing laboratory geochemical analyses including at least one of x-ray fluorescence (XRF), x-ray diffraction (XRD) and inductively coupled plasma mass spectrometry (ICP). In some cases, measuring formation acoustic velocities for the target wells comprises logging the target wells to measure at least two of P-wave velocity (Vp), S-wave velocity (Vs), compressional wave slowness (DTC), and shear wave travel time (DTS).

In some embodiments, generating the characteristic log signatures for the different lithostratigraphic layers comprises identifying characteristic rock changes using geochemical properties of the matrix cross-plots and histograms.

In one aspect, systems for characterization reservoirs by identification of lithostratigraphic layers within a subterranean formation based on rock geochemistry of the subterranean formation include: a statistics module operable to:

correlate data from non-target wells on type charts of characteristic rock sample and log signature patterns for different lithostratigraphic layers, the patterns generated based on the measured geochemical/mineralogical parameters and acoustic velocities associated with the different lithostratigraphic layers identified in the target wells; iteratively select a next type chart and associated data based on a user selection of a match on a previous type chart until a single lithostratigraphy is identified; a display receiving data from the statistics module to present data from non-target wells on type charts of characteristic rock sample and log signature patterns; and a plotting module operable to associate the single lithostratigraphy with specific depths and data from the non-target well, passes the association back to the database.

These systems can include one or more of the following features.

In some embodiments, the statistics module receives type charts and rankings of a lithostratigraphic model and the data of the non-target wells from a database. In some cases, data of the non-target wells includes geochemical or mineralogical parameters for the non-target wells. In some cases, data of the non-target wells includes natural and neutron activated gamma ray elemental spectrometry spectroscopy and acoustic slowness data measured using downhole logging tools.

The approach described in this specification can provide an interpretation of subsurface lithostratigraphy using well logs with drastically reduced turnaround time independently from core or biostratigraphic data. In particular, this approach can fit well log data from targeted wells to provide a tool to derisk reservoir delineation and improve subsurface mapping of different reservoirs.

The details of one or more embodiments of these systems and methods are set forth in the accompanying drawings and the description below. Other features, objects, and advantages of these systems and methods will be apparent from the description and drawings, and from the claims.

DESCRIPTION OF DRAWINGS

The patent or application file contains at least one color drawing executed in color. Copies of this patent or patent application publication with one or more color drawings-drawing(s) will be provided by the Patent and Trademark Office upon request and payment of the necessary fee.

Like reference symbols in the various drawings indicate like elements.

DETAILED DESCRIPTION

This specification describes an approach using geochemical and other rock measurements from rock samples including X-Ray diffraction, X-Ray fluorescence and inductively coupled plasma spectrometry in context of their lithostratigraphic assignment to perform pattern identification. Based on these patterns, wellbore signals (e.g., neutron capture gamma ray spectroscopy, natural gamma ray spectroscopy and sonic acoustic velocity signals) are used to identify and interpret subsurface rock formations. This approach uses core-based sedimentological observations and links them to wellbore measurements in order to interpret lithostratigraphic intervals that are otherwise undistinguishable without core samples or biostratigraphy data.

This approach enables petrophysical explorations to distinguish between sedimentary deposits of economic viability with different age and variable reservoir characteristics that share similar rock properties in the subsurface when measured using conventional wellbore or lab measurements on the rocks. By reducing the need for capturing and retrieving rock samples to the surface, this approach can reduce the cost and the turnaround time associated with core sampling while also reducing the uncertainty for subsurface reservoir characterization and mapping associated with limited differentiation between formations with similar characteristics.

Figure 1:
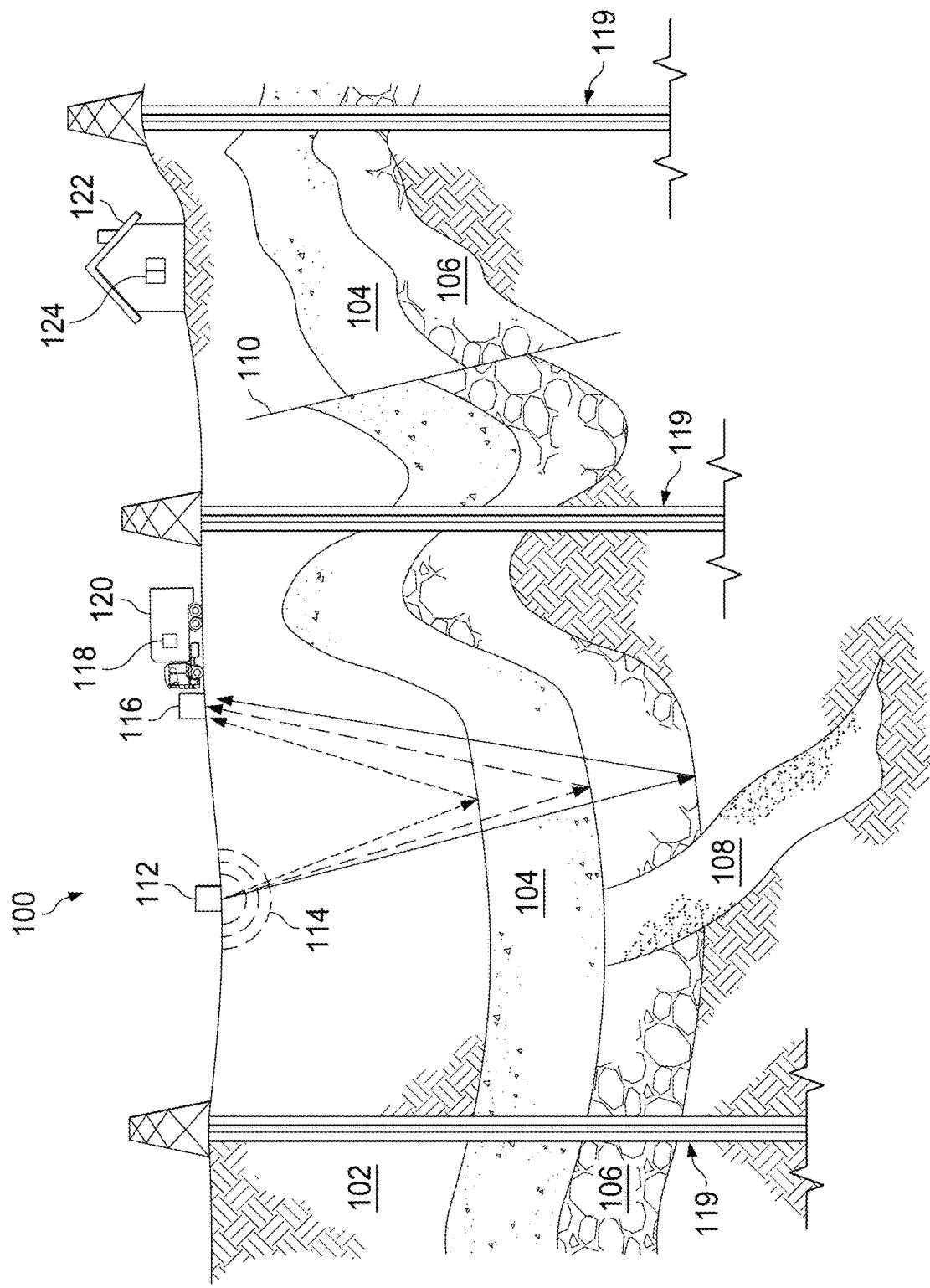
FIG. 1 is a schematic view of a survey being performed to map subterranean features such as sedimentary layers or reservoirs.

FIG. 1 is a schematic view of a petrophysical survey being performed to map subterranean features such as sedimentary layers or reservoirs in a subterranean formation 100. Cable conveyed logging 121 tools send different signals 125 into the formation that interact with the rocks and fluids in the formation. The formation emits a signal back that is measured by a tool receiver 123 (e.g., for neutron capture gamma ray spectroscopy and sound velocity slowness). Other tools passively measure the rock signals without a source in the tool, such as natural gamma ray spectroscopy, which measures natural rock radiation. This data is then used as input to correctly define the reservoirs by using the generated LINS model. The subterranean formation 100 includes a layer of impermeable cap rocks 102 at the surface and underlying layers 104, 106, and 108. A fault line 110 extends across the layer 104 and the layer 106.

Identifying and distinguishing between the layers 104, 106, and 108 can be important to assessing and managing a hydrocarbon reservoir. Some information about the transitions between layers can be obtained by seismic surveys in which a seismic source 112 (for example, a seismic vibrator or an explosion) generates seismic waves 114 that propagate in the earth. The velocity of these seismic waves depends properties such as, for example, density, porosity, and fluid content of the medium through which the seismic waves are traveling. Different geologic bodies or layers in the earth are distinguishable because the layers have different properties and, thus, different characteristic seismic velocities. As the seismic waves 114 contact interfaces between geologic bodies or layers that have different velocities, the interface reflects some of the energy of the seismic wave and refracts part of the energy of the seismic wave. Such interfaces are sometimes referred to as horizons.

The seismic waves 114 are received by a sensor or sensors 116. Although illustrated as a single component in FIG. 1, the sensor or sensors 116 are typically a line or an array of sensors 116 that generate an output signal in response to received seismic waves including waves reflected by the horizons in the subterranean formation 100. The sensors 116 can be geophone-receivers that produce electrical output signals transmitted as input data, for example, to a computer 118 on a seismic control truck 120. Based on the input data, the computer 118 may generate a seismic data output such as, for example, a seismic two-way response time plot.

Well logging, core sampling, and cuttings analysis associated with wells 119 extending through the layers can be used to provide detailed information about these layers. In particular, reservoir assessment and management relies on accurate identification and differentiation of these underlying layers. Core sampling cuttings analysis and well logging typically provide the most accurate data for identifying and interpreting stratigraphic intervals, but geochemical core and cuttings analysis are expensive and time consuming. This specification describes an approach using geochemical and other rock measurements from rock samples including X-Ray diffraction, X-Ray fluorescence and inductively coupled plasma spectrometry in context of their lithostratigraphic assignment to perform pattern identification and then to propagate those patterns to wellbore geochemical logs for more rapid application. Wellbore signals are then used to identify and interpret subsurface rock formations. This approach uses core-based sedimentological/geochemical observations and links them to wellbore measurements in order to interpret lithostratigraphic intervals that are otherwise indistinguishable without core samples or biostratigraphy data.

A control center 122 can be operatively coupled to the seismic control truck 120 and other data acquisition and wellsite systems. The control center 122 may have computer facilities for receiving, storing, processing, and/or analyzing data from the seismic control truck 120 and other data acquisition and wellsite systems. For example, computer systems 124 in the control center 122 can be configured to analyze, model, control, optimize, or perform management tasks of field operations associated with development and production of resources such as oil and gas from the subterranean formation 100. Alternatively, the computer systems 124 can be located in a different location than the control center 122. Some computer systems are provided with functionality for manipulating and analyzing the data, such as performing seismic interpretation or borehole resistivity image log interpretation to identify geological surfaces in the subterranean formation or performing simulation, planning, and optimization of production operations of the wellsite systems.

Figure 2:
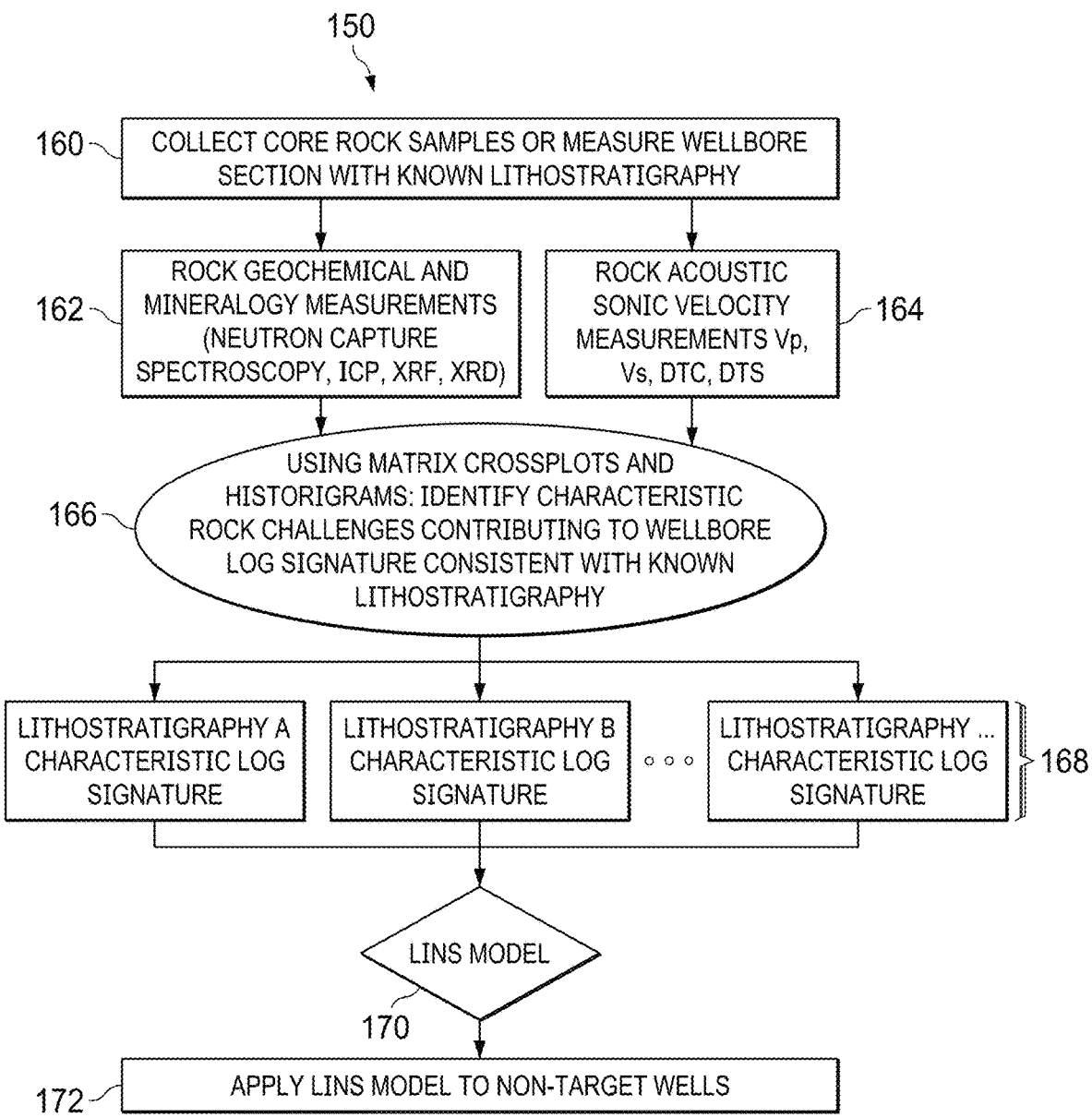
FIG. 2 is a flowchart of an approach to constructing a lithographic interpretation using a lithostratigraphic interpretation using neutron capture spectroscopy (LINS) model using rock samples or wellbore measurements.

FIG. 2 illustrates an approach to reservoir characterization by identification of lithostratigraphic layers within a subterranean formation based on rock geochemistry of the subterranean formation. The approach uses a method 150 to construct and apply a LINS model using rock samples or wellbore measurements (FIG. 2). The method 150 begins by collecting the lithostratigraphic information of target wells (step 160). This collection can be done by approaches including collecting core rock samples as target wells are being drilled, collecting wireline signals controlled by rock geochemical and geomechanical behavior, or by receiving previously measured lithostratigraphic profiles for previously drilled target wells. Target wells are typically chosen to represent different geographic areas of the reservoir and to include multiple samples from lithostratigraphic layers present within the subterranean formation.

Geochemical/mineralogical parameters of the target wells are measured at different depths in the target wells (step 162). Rock samples geochemical analysis by using X-Ray fluorescence (XRF) or inductively coupled plasma spectrometry (ICP) can yield 50 elements (see, e.g., table below) which include major elements such as silicon, aluminum, titanium, potassium, and others) and minor elements such as rare earth elements (examples include: Lanthanum, Gadolinium and others).

| Element | Unit |
|---------|------|
| Si | wt % |
| Al | wt % |
| Ca | wt % |
| Mg | wt % |
| Fe | wt % |
| Ti | wt % |
| K | wt % |
| Mn | wt % |
| Na | wt % |
| P | wt % |
| S | wt % |
| Ba* | ppm |
| Be | ppm |
| Ho | ppm |
| La | ppm |
| Lu | ppm |
| Mo | ppm |
| Nb | ppm |
| Nd | ppm |
| Ni | ppm |
| Pb | ppm |
| Pr | ppm |
| Rb | ppm |
| Sc | ppm |
| Sm | ppm |
| Sn | ppm |
| Br | ppm |
| Ce | ppm |
| Co | ppm |
| Cr | ppm |
| Cs | ppm |
| Cu | ppm |
| Dy | ppm |
| Er | ppm |
| Eu | ppm |
| Ga | ppm |
| Gd | ppm |
| Hf | ppm |
| Sr | ppm |
| Ta | ppm |
| Tb | ppm |
| Th | ppm |
| Tm | ppm |
| U | ppm |
| V | ppm |
| W | ppm |
| Y | ppm |
| Yb | ppm |
| Zn | ppm |
| Zr | ppm |

Similarly, measuring geochemical or mineralogical parameters for the target wells can include performing downhole logging of the target wells. However, downhole measurements can investigate only smaller number of elements (including silicon, aluminum, potassium, calcium, magnesium, titanium, sulfur, gadolinium, iron, manganese, and others). Natural radioactive gamma ray spectroscopy tools can be used to investigate the elements thorium, potassium and uranium. Acoustic velocity slowness and total neutron capture cross section (sigma) are other parameters that can be measured by downhole logging tools and are likely to be used in this approach. Measuring geochemical or mineralogical parameters for the target wells can also or alternatively include performing analysis of cuttings taken from the target wells with much higher depth uncertainty. For example, performing analysis of cuttings taken from the target wells can include performing x-ray fluorescence (XRF), x-ray diffraction (XRD) and inductively coupled plasma mass spectrometry (ICP). This measurement can be done by approaches including performing the measurement as target wells are being drilled or by receiving previously measured geochemical or mineralogical parameters for previously drilled target wells.

Formation acoustic velocities of the target wells are measured at different depths in the target wells (step 164). Both compressional wave slowness (DTC), and shear wave travel time (DTS) as well as other derivatives of the same measurements can be employed to infer characteristic changes pertaining to the lithostratigraphic layers in question. Measuring acoustic velocities for the target wells can include performing downhole logging of the target wells. Measuring formation acoustic velocities for the target wells can include logging the target wells to measure at least two of P-wave velocity (Vp), S-wave velocity (Vs), compressional wave slowness (DTC), and shear wave travel time (DTS). This measurement can be done by approaches including performing the measurement as target wells are being drilled or by receiving previously measured acoustic velocities for previously drilled target wells. Quality control checks are performed on the data. If valid, the data is analyzed and forms the basis of or input to the LINS model. If not valid, the data is corrected or new data is collected.

Characteristic log signatures for different lithostratigraphic layers are generated based on the measured geochemical/mineralogical parameters and acoustic velocities associated with the different lithostratigraphic layers identified in the target wells (step 168). Generating the characteristic log signatures for the different lithostratigraphic layers can include identifying characteristic rock changes using matrix cross-plots and histograms. This is done by carefully investigating multiple signals that may show consistent signal response or signal across a common reservoir or lithostratigraphic layer (method 350). LINS approach invests heavily on mapping out sample grouping with common trend-lines on crossplots where a function representing each trend-line can be calculated to guide the lithostratigraphic interpretation. An alternative approach may be to use cluster analysis supervised by known lithostratigraphy using software designed for well log analysis and core data analysis—a set of lithostratigraphic control wells with defined intervals E1, D1, R are the kernel.

The characteristic log signatures for the different lithostratigraphic layers are then combined into a LINS model (step 170). LINS model is a tool that analysts can easily plot data on a series of crossplots for use to semi-quantitatively distinguish between the different reservoirs or lithostratigraphic units. This can be done using statistical software capable of generating histograms and crossplots.

The initial LINS model is validated by performing a field blind test with a pre-established outcome. If the results match the validation data set, the model is finalized and applied to non-target wells. If the results are inconclusive or do not match the validation data set, the data is corrected or new data is collected (e.g., from additional target wells).

The LINS model is then used to identify lithostratigraphic layers within the subterranean formation by applying the LINS model to logs of non-target wells (step 172). The process of applying a LINS model to logs of non-target wells is described in more detail with respect to FIGS. 4 and 5.

The characteristic log signatures for the different lithostratigraphic layers are then combined into a LINS model (step 170). LINS model is a tool that analysts can easily plot data on a series of crossplots to use to semi-quantitatively distinguish between the different reservoirs or lithostratigraphic units. This can be done using statistical software capable of generating histograms and crossplots.

Figure 3:
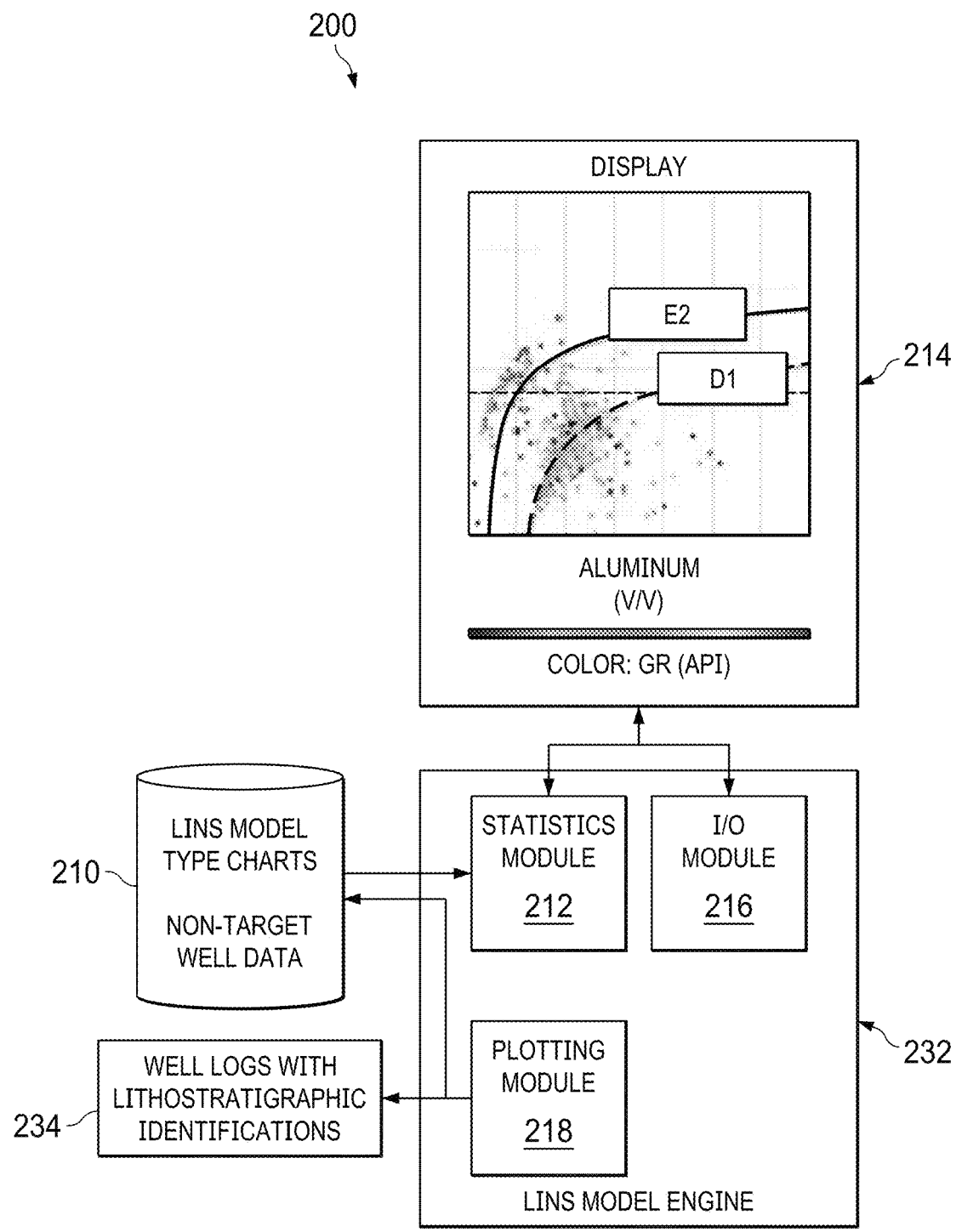
FIG. 3 is a block diagram of an approach to generating an exemplary LINS model.

FIG. 3 is a block diagram of an exemplary implementation of a LINS model system 200. The type charts of the model and the data from the non-target wells is stored on a database 210. The LINS model engine includes a statistics module 212 that receives that generates crossplots of data from a non-target well on a type chart. An example of how these crossplots and type chart are used to identify lithostratigraphic layers is described with respect to FIG. 4. The initial type chart and data are presented on a display 214 which allows an analyst to use an input/output (I/O) module 216 to select which of two profiles the data most closely matches. The selection triggers the statistics module 212 to present a crossplot and type chart that differentiates between the data sets that match the selected profile. After a series of choices match the data to a specific lithostratigraphy, the statistics module 212 passes the identification and non-target well data to a plotting module 218 that associates the identified lithostratigraphy with specific depths and data from the non-target well, passes the association back to the database, and generates a well log that includes the identified lithostratigraphy(ies) and the non-target well data (see, e.g., FIG. 6).

Figure 4:
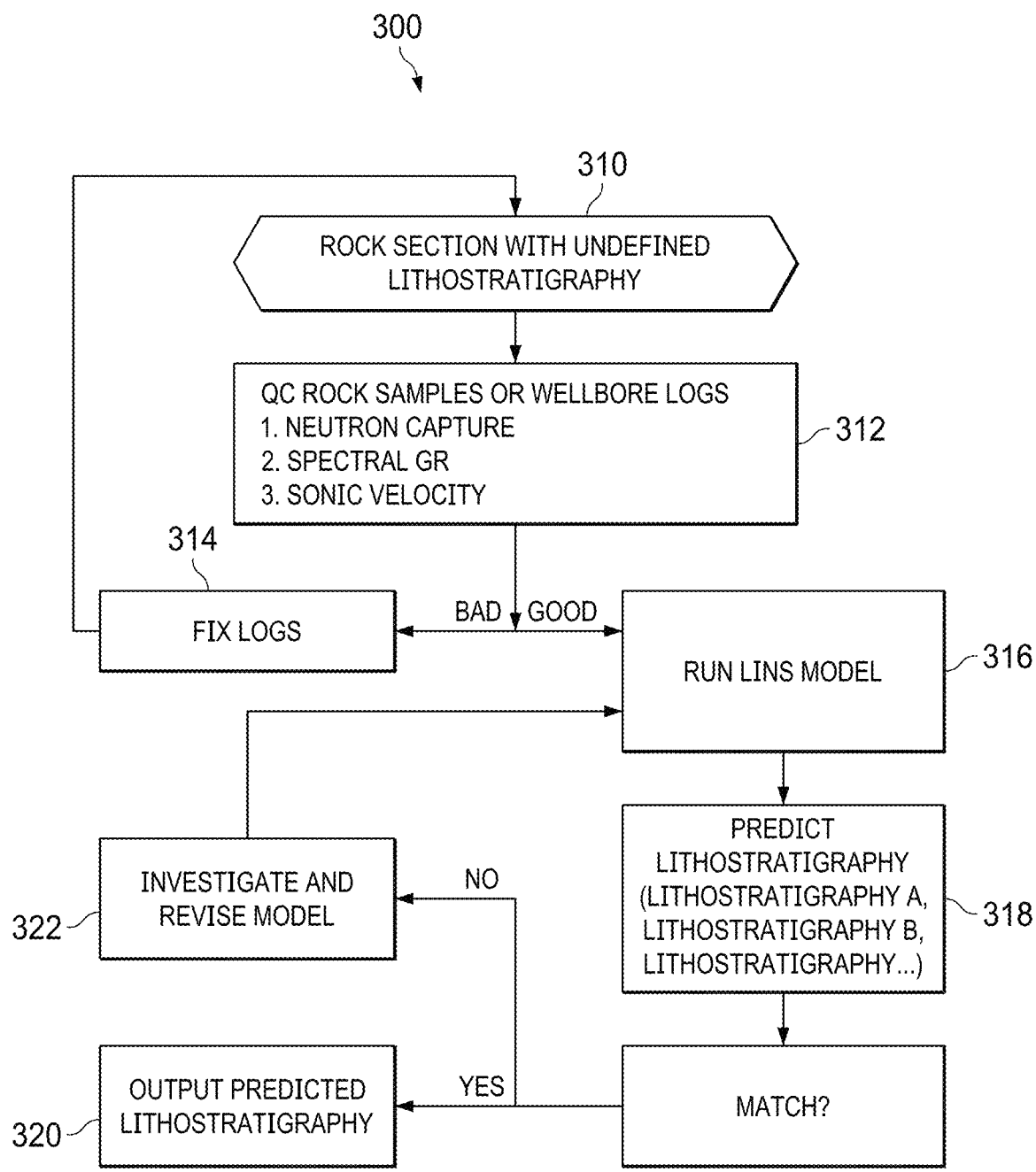
FIG. 4 is a flowchart of an approach to applying a LINS model to rock sections with unknown lithostratigraphy
Figure 5:
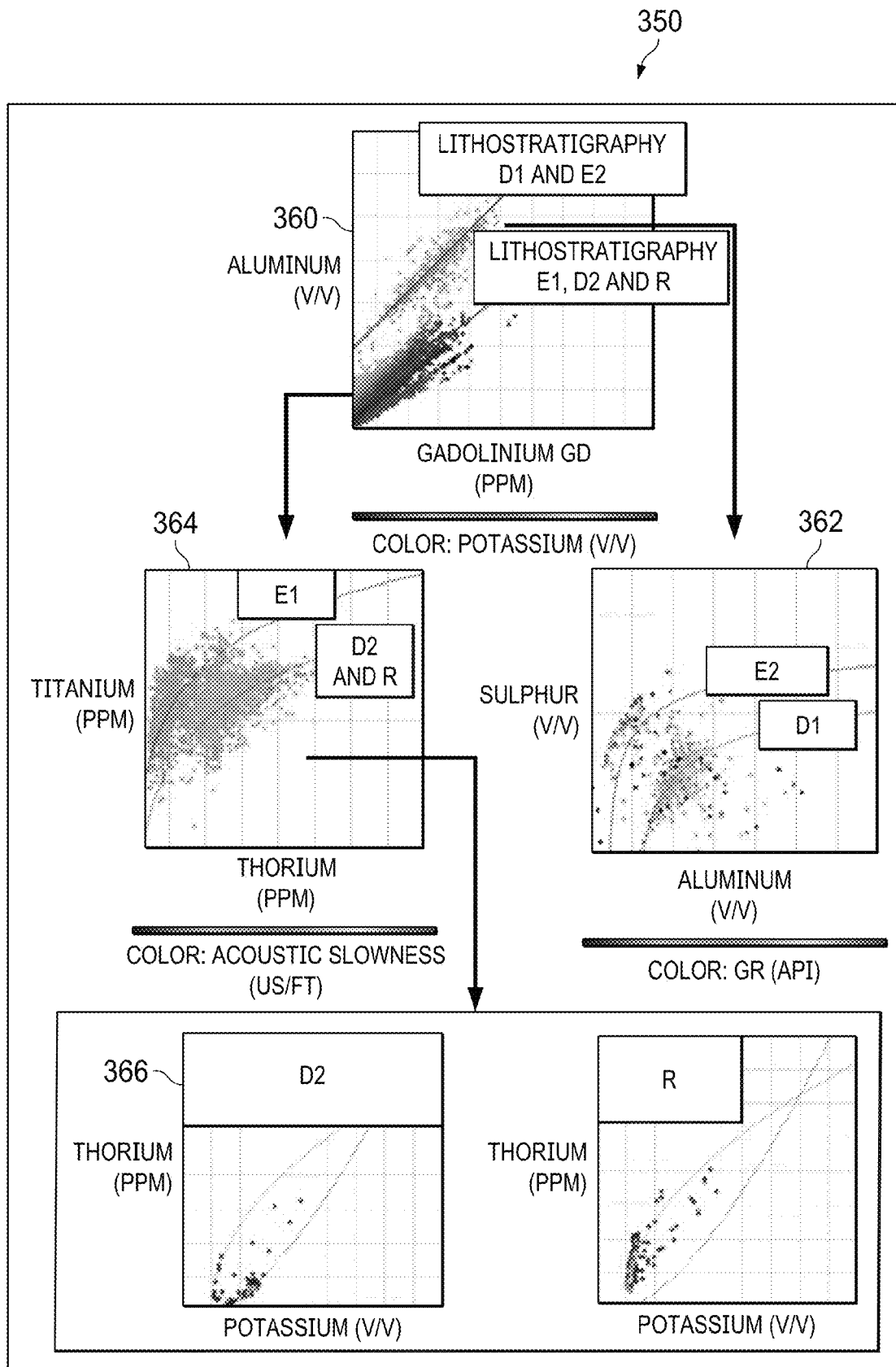
FIG. 5 is a schematic illustrating application of a prototype LINS model to an example formation.

FIG. 4 is a flowchart of an approach (method 300) to applying a LINS model to rock sections with unknown lithostratigraphy. The method 300 can be applied to a rock section with an undefined lithostratigraphy (step 310). For example, the data can include measured parameters of rock samples, well logs, or both. Quality control checks are performed on the input data (step 312). The input data are checked to verify that they fall within normal expected data population range and if it is within acceptable noise levels. If the input data fails the quality control checks, the logs are fixed or discarded (step 314). This is done on case-by-case basis. For example, data can be normalized to correct data range or re-measured either at wellsite or at the lab (for rock samples). If the input data passes the quality control checks, the LINS model (for example, the LINS model 200 described with respect to FIG. 3) is run on the input data (step 316) to predict the lithostratigraphy (step 318) by comparing the input data associated with the rock section with an undefined lithostratigraphy to the characteristic log signatures included in the LINS model. If the input data matches one of the characteristic log signatures, the predicted lithostratigraphy is provided as output (step 320). The shallowest depth of the defined lithostratigraphy unit is recorded as the top of the reservoir or unit. If the input data does not match one of the characteristic log signatures, additional investigation is performed and the model is revised and updated based on the results of the additional investigation (step 322). If the LINS model fails to predict a valid output, additional data is gathered through lab or wellsite measurements to obtain more information about the unidentified zone, which later becomes part of the updated LINS model for future wells FIG. 5 is a schematic illustrating application of a prototype LINS model to rock sections from a subterranean formation with 5 specific lithostratigraphy layers (i.e., lithostratigraphy D1, lithostratigraphy D2, lithostratigraphy E1, lithostratigraphy E2, and lithostratigraphy R). These are generic symbols used to represent different reservoirs or lithostratigraphic units in the data set used to test the prototype. The prototype LINS model was generated by applying the method described with respect to FIG. 2 to data from a number of additional wells with known lithostratigraphy. Seven key data from these wells included (1) concentrations of aluminum, gadolinium, potassium, thorium, titanium, and sulphur, (2) acoustic slowness, and (3) color at different distances downhole in the additional wells. The method is a geological insight guided principal components identification by successive iteration. All log or lab measurements that have the tendency to capture changes controlled by geochemistry or geomechanics of the reservoirs or lithostratigraphic units are investigated in 200 to conclude which parameters demonstrate the highest correlation to the predefined lithostratigraphy. This process is explained in FIG. 4. The depths at which these parameters were measured and the known depths of the specific lithostratigraphic layers provided an association between the values of these parameters and the specific lithostratigraphic layers. The prototype LINS model used the 7 key inputs and five type charts (FIG. 5) to differentiate between the target stratigraphic layers E1, E2, D1, D2, R.

In method 350, a first signature pattern 360 is the relationship between aluminum, gadolinium, and potassium levels. The first signature pattern 360 is displayed as plot of aluminum in units of weight/weight (w/w) and gadolinium in units of parts per million (ppm). Potassium (w/w) is represented as a colored third dimension as the color of each data point. This signature pattern 360 provided a clear differentiation between lithostratigraphy layers D1 and E2 and lithostratigraphy layers E1, D2, and R. Lithostratigraphy layers D1 and E2 had higher aluminum concentrations for given gadolinium concentrations than lithostratigraphy layers E1, D2, and R. In addition, lithostratigraphy layers E1, D2, and R had negligible levels of potassium while lithostratigraphy layers D1 and E2 display higher potassium levels. The values have to be considered relative to each cluster/group in general, but in this specific example, potassium range is 0-0.045 w/w and for aluminum 0-0.07 w/w. Human geological insight guided principal components identification by successive iteration. The differentiation was performed manually by an analyst. Due to the inherited variability in data ranges and noise levels triggered by different tool design and processing, automating this process will make it prone to false, unrepresentative clustering.

A second signature pattern 362 uses the relationship between aluminum and sulphur levels. The second signature 362 is displayed as plot of aluminum (w/w) and sulphur (w/w). Gamma ray is presented as color third dimension to separate the D1 from the E2. The second signature pattern 362 provided a clear differentiation between lithostratigraphy layer D1 and lithostratigraphy layer E2. Lithostratigraphy layer E2 had higher sulphur concentrations for given aluminum concentrations than lithostratigraphy layers D1. In addition, E2 group displays lower Gamma Ray (GR) values than the D1 group. The color for each data point is the level of the total natural radioactivity (GR) of each data point.

A third signature pattern 364 is the relationship between titanium and thorium levels and acoustic slowness on the third dimension color scale. The third signature 364 is displayed as plot of titanium (ppm) and thorium (ppm). Certain elements such as titanium, thorium and gadolinium are present in rocks only in dilute levels, therefore are reported in ppm rather than w/w or v/v compared to elements such as silicon or aluminum which are abundant in natural rocks. Acoustic slowness in units of microseconds per foot (µs/ft) is represented as a third dimension using the color of each data point. The third signature pattern 364 provides a clear differentiation between lithostratigraphy layer E1 and lithostratigraphy layers D2 and R. Lithostratigraphy layer E1 tended to have higher titanium concentrations for given thorium concentrations than lithostratigraphy layers D2 and R. In addition, Lithostratigraphy layer E1 tended to have acoustic slowness of about 75 µs/ft while lithostratigraphy layers D2 and R tended to acoustic slowness of about 60 µs/ft.

A fourth signature pattern 366 is the relationship between thorium and potassium levels. The fourth signature pattern 366 is displayed as plot of thorium (ppm) and potassium (w/w). The fourth signature pattern 366 provided a differentiation between lithostratigraphy layer D2 and lithostratigraphy layer R. Lithostratigraphy layer R tended to have higher thorium concentrations for given potassium concentrations than lithostratigraphy layer D2.

After development of the signatures and combination of these signatures into the prototype LINS model, the prototype LINS model was tested in four other wells as a blind test. The prototype LINS model was run to identify lithostratigraphic layers in these four other wells and the model output was compared to lithostratigraphic layers as identified by core samples obtained from the same wells.

Figure 6:
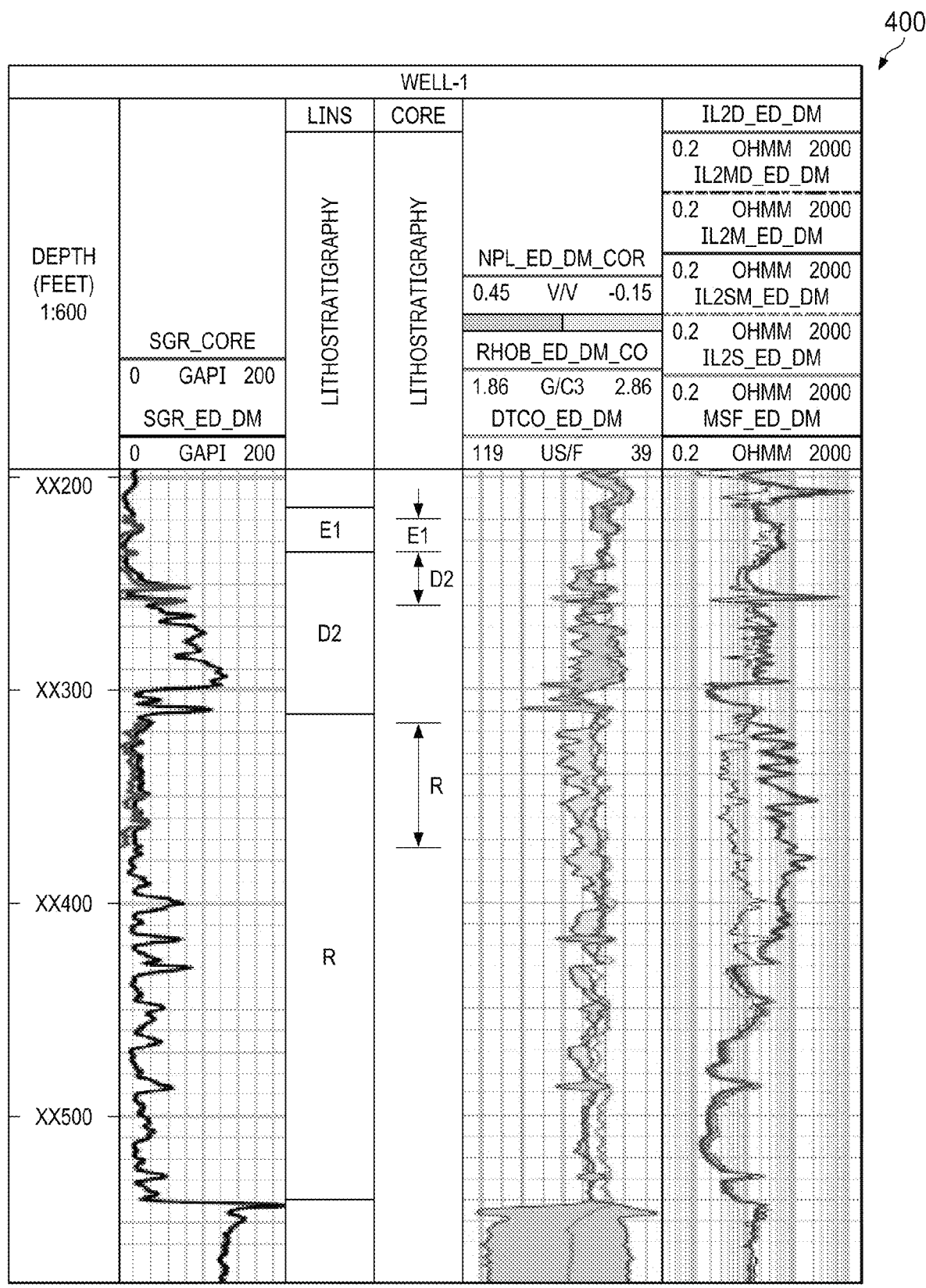
FIG. 6 is a well log comparing lithostratigraphy of the well as estimated using a LINS model with lithostratigraphy of the well based on analysis of the core samples as a blind field test which confirmed the model validity

FIG. 6 is a well log 400 comparing lithostratigraphy of the well as estimated using the prototype LINS model with lithostratigraphy of the well based on analysis of the core samples.

Figure 7:
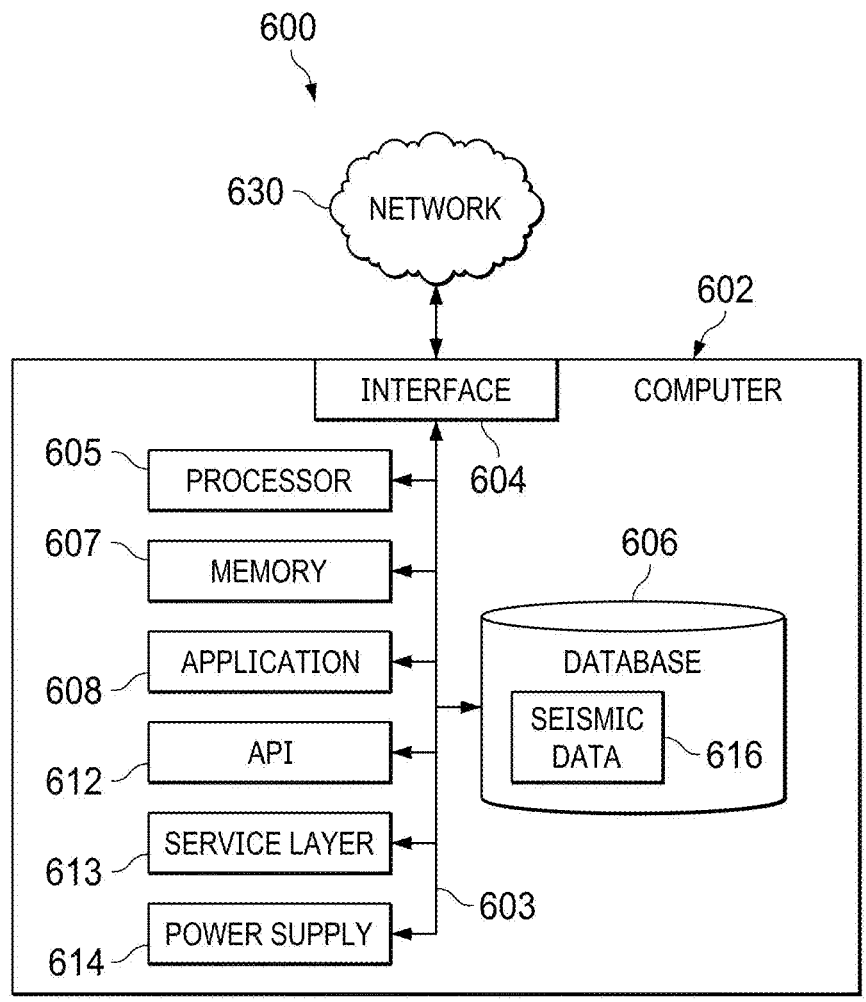
FIG. 7 is a block diagram illustrating an example computer system used to provide computational functionalities associated with described algorithms, methods, functions, processes, flows, and procedures according to some implementations of the present disclosure.

FIG. 7 is a block diagram of an example computer system 600 used to provide computational functionalities associated with described algorithms, methods, functions, processes, flows, and procedures described in the present disclosure, according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a high level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both), over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 6, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 6, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A method for reservoir characterization by identification of lithostratigraphic layers within a subterranean formation based on rock geochemistry of the subterranean formation, the method comprising:
   collecting rock samples related to lithostratigraphy of target wells in the subterranean formation;
   measuring geochemical/mineralogical parameters of the rock samples with laboratory equipment;
   measuring geochemical/mineralogical parameters of the subsurface formation using wellbore geochemical logging tools in the target wells;
   measuring formation acoustic velocities for the target wells;

generating characteristic rock sample and log signature patterns for different lithostratigraphic layers based on the measured geochemical/mineralogical parameters and acoustic velocities associated with the different lithostratigraphic layers identified in the target wells;

combining the characteristic log signatures for the different lithostratigraphic layers into a lithographic interpretation using neutron capture spectroscopy (LINS) model; and identifying the lithostratigraphic layers within the subterranean formation by applying the LINS model to well logs of non-target wells.

2. The method of claim 1, wherein generating the characteristic log signatures for the different lithostratigraphic layers comprises identifying characteristic rock changes using matrix cross-plots and histograms.

3. The method of claim 1, wherein collecting the lithostratigraphy of targeted wells in the subterranean formation comprises collecting core rock samples from at least some of the targeted wells.

4. The method of claim 3, wherein collecting the lithostratigraphy of targeted wells in the subterranean formation comprises receiving previously measured lithostratigraphic profiles for previously drilled target wells.

5. The method of claim 1, wherein measuring geochemical or mineralogical parameters for the target wells comprises logging the target wells.

6. The method of claim 5, wherein logging the target wells comprises using downhole logging tools to measure geochemical properties by natural and neutron activated gamma ray elemental spectrometry spectroscopy and acoustic slowness.

7. The method of claim 5, wherein measuring geochemical or mineralogical parameters for the target wells further comprises performing analysis of cuttings taken from the target wells.

8. The method of claim 5, wherein performing analysis of cuttings taken from the target wells comprises performing laboratory geochemical analyses including at least one of x-ray fluorescence (XRF), x-ray diffraction (XRD) and inductively coupled plasma mass spectrometry (ICP).

9. The method of claim 5, wherein measuring formation acoustic velocities for the target wells comprises logging the target wells to measure at least two of P-wave velocity (Vp), S-wave velocity (Vs), compressional wave slowness (DTC), and shear wave travel time (DTS).

10. A method for reservoir characterization by identification of lithostratigraphic layers within a subterranean formation based on rock geochemistry of the subterranean formation, the method comprising:

collecting rock samples related to lithostratigraphy of target wells in the subterranean formation;

measuring formation acoustic velocities for the target wells;

generating characteristic rock sample and log signature patterns for different lithostratigraphic layers based on the measured geochemical / mineralogical parameters and acoustic velocities associated with the different lithostratigraphic layers identified in the target wells;

combining the characteristic log signatures for the different lithostratigraphic layers into a lithographic interpretation using neutron capture spectroscopy (LINS) model; and identifying the lithostratigraphic layers within the subterranean formation by applying the LINS model to well logs of non-target wells.

11. The method of claim 10, further comprising measuring geochemical/ mineralogical parameters of the rock samples with laboratory equipment.

12. The method of claim 11, further comprising measuring geochemical/ mineralogical parameters of the subsurface formation using wellbore geochemical logging tools in the target wells.

13. The method of claim 12, wherein measuring geochemical/mineralogical parameters of the subsurface formation comprises using downhole logging tools to measure geochemical properties by natural and neutron activated gamma ray elemental spectrometry spectroscopy and acoustic slowness.

14. The method of claim 13, wherein performing analysis of cuttings taken from the target wells comprises performing laboratory geochemical analyses including at least one of x-ray fluorescence (XRF), x-ray diffraction (XRD) and inductively coupled plasma mass spectrometry (ICP).

15. The method of claim 14, wherein measuring formation acoustic velocities for the target wells comprises logging the target wells to measure at least two of P-wave velocity (Vp), S-wave velocity (Vs), compressional wave slowness (DTC), and shear wave travel time (DTS).

16. The method of claim 15, wherein generating the characteristic log signatures for the different lithostratigraphic layers comprises identifying characteristic rock changes using matrix cross-plots and histograms.

* * * * *